United States Patent [19]
Dean et al.

[11] Patent Number: 5,830,433
[45] Date of Patent: Nov. 3, 1998

[54] RADIOLABELED GROWTH HORMONE SECRETAGOGUE

[75] Inventors: Dennis C. Dean, Chatham; David G. Melillo, Scotch Plains; Ravi Nargund, East Brunswick; Leonardus Van Der Ploeg, Scotch Plains; Sheng-Shung Pong, Edison; James M. Schaeffer; Roy G. Smith, both of Westfield, all of N.J.

[73] Assignee: Merck & Co., Inc., Rahway, N.J.

[21] Appl. No.: 768,368

[22] Filed: Dec. 17, 1996

Related U.S. Application Data

[60] Provisional application No. 60/008,961 Dec. 20, 1995.
[51] Int. Cl.$^6$ .................. A61K 51/00; C07D 471/10
[52] U.S. Cl. .............................. 424/1.81; 546/17
[58] Field of Search ................... 424/1.81; 546/17

[56] References Cited

U.S. PATENT DOCUMENTS

| | | | |
|---|---|---|---|
| 4,120,945 | 10/1978 | Gutcho et al. | 436/531 |
| 4,839,344 | 6/1989 | Bowers et al. | 514/16 |
| 5,536,716 | 7/1996 | Chen et al. | 514/215 |

FOREIGN PATENT DOCUMENTS

WO 94/13696  6/1994  WIPO.

OTHER PUBLICATIONS

Seifert, H., et al, *Nature*, vol. 313, pp. 487–489 (1985).

M.J. Puchner, et al., *Database Medline on STN*, No. 92339760, abstract of Mol. and Cell. Endocrinol., vol. 85 (3), 1992.

W. Odell, *Radiopharmacy*, pp. 833–859, 1972, "Principles of Competitive Binding Assays".

P.W. Horton, et al., *Radionuclide Techniques in Clinical Investigation*, pp. 161–163, 1982.

D. C. Dean, et al., *J. Med. Chem.*, vol. 39, No. 9, pp. 1767–1770 (1996) "Development of a High Specific Activity Sulfur–35–Labeled Sulfonamide Radioligand That Allowed the Identification of a New Growth Hormone Secretagogue Receptor".

A.D. Howard, et al., *Science*, vol. 273 (Aug. 16, 1996) pp. 974–977 "A Receptor in Pituitary and Hypothalamus that Functions in Growth Hormone Release".

A. A. Patchett, et al., *Proc. natl. Acad. Sci. USA*, vol. 92, pp. 7001–7005, Jul. 1995, Design and biological activities of L–163,191 (MK–0677): A potent, orally active growth hormone secretagoue.

R. G. Smith, et al., *Science*, vol. 260, Jun. 11, 1993, pp. 1640–1643, "A Nonpeptidyl Growth Hormone Secretagogue".

*Primary Examiner*—Alan L. Rotman
*Attorney, Agent, or Firm*—J. Eric Thies; David L. Rose

[57] ABSTRACT

The present invention is directed to [$^{35}$S]-N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide, and pharmaceutically acceptable salts thereof. This [$^{35}$S] radioligand is useful in identifying and characterizing cellular receptors which play a role in the activity of growth hormone secretatogogues. In addition, this [$^{35}$S] radioligand is useful in assays which test compounds for growth hormone secretagogue activity.

12 Claims, No Drawings

RADIOLABELED GROWTH HORMONE SECRETAGOGUE

CROSS REFERENCE TO RELATED APPLICATIONS

This application claims priority under 35 U.S.C. §119(e) from U.S. Ser. No. 60/008,961, filed Dec. 20, 1995.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk of transmission of a disease associated with the source of the pituitary gland. Recombinant growth hormone has become available which, while no longer carrying any risk of disease transmission, is still a very expensive product which must be given by injection or by a nasal spray.

Other compounds have been developed which stimulate the release of endogenous growth hormone. The use of such agents which stimulate the pulsitile release of growth hormone would be a significant advance in the treatment, for example, of growth hormone deficiency in children and adults. Compounds possessing growth hormone secretagogue activity are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Patent No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; U.S. Pat. No. 5,536,716; EPO Patent Pub. No. 0,144,230; EPO Patent Pub. No. 0,513,974; EPO Patent Pub. No. 0,659,179; PCT Patent Pub. No. WO 94/05634; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; *Science,* 260, 1640–1643 (Jun. 11, 1993); *Ann. Rep. Med. Chem.,* 28, 177–186 (1993); *Bioorg. Med. Chem. Ltrs.,* 4(22), 2709–2714 (1994); and *Proc. Natl. Acad. Sci. USA,* 92, 7001–7005 (July 1995). By the term "growth hormone secretagogue" (GHS) is meant any compound or agent that directly or indirectly stimulates or increases the release of growth hormone in an animal.

Growth hormone secretagogues (especially a growth hormone secretagogue bearing a radiolabel) are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, growth hormone secretagogues are useful in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. Growth hormone secretagogues may also be employed to investigate the possible negative or positive feedback effects of some of the pituitary hormones, e.g., growth hormone and endorphin peptides, on the pituitary to modify growth hormone release. Of particular scientific importance is the use of growth hormone secretagogues to elucidate the subcellular mechanisms mediating the release of growth hormone.

Methodology is known in the art to determine the activity of a compound as a growth hormone secretagogue. For example, an ex vivo assay is described by Smith, et al., *Science,* 260, 1640–1643 (1993) (see text of FIG. 2 therein), but this assay requires the use of cell cultures and does not give an indication of competitive binding activity.

Accordingly, it would be desirable to develop a radioligand which can be used to identify and characterize cellular receptors which play a role in the activity of growth hormone secretatogues. It would also be desirable to have a radioligand available for use in an assay for testing compounds for growth hormone secretagogue activity.

Such studies normally require a high specific activity radioligand. Previous attempts to develop a binding assay using [$^3$H]-labeled or [$^{125}$I]-labeled peptide ligands derived from GHRP-6 met with limited success. See R. F. Walker, et al. *Neuropharmacol* 1989, 28, 1139 and C. Y. Bowers,et al., *Biochem. Biophy. Res. Comm.* 1991, 178, 31. Generally, the binding of such peptide ligands was of low affinity and of excessively high capacity. Moreover, the binding affinities did not correlate with the growth hormone secretory activity of the peptides. The lack of correlation of binding and growth hormone secretory activity most likely was the result of the relatively low specific activity (in the case of [$^3$H] GHRP-6) and non-specific binding properties of the radioligands. Accordingly, there is a need in the art for radiolabeled compounds which stimulate the release of endogenous growth hormone and possess high specific radiochemical activity.

Certain spiro compounds are disclosed in U.S. Pat. No. 5,536,716, PCT Patent Publication WO 94/13696 and *Proc.*

*Natl. Acad. Sci. USA*, 92, 7001–7005 (July 1995) as being non-peptidal growth hormone secretagogues. These compounds have the ability to stimulate the release of natural or endogenous growth hormone. Among the preferred compounds disclosed therein is N-[1(R)-[(1,2-dihydro-1-methanesulfonylspiro[3H-indole-3,4'-piperidin]-1'-yl) carbonyl]-2-(phenylmethyloxy)ethyl]-2-amino-2-methylpropanamide. Due to its high growth hormone secretatory activity, this compound was selected for preparation as a radioligand.

Generally, in situations where specific activity >100 Ci/mmol is required, radioiodine is the label of choice for the study of receptors. See K. G. McFarthing, In *Receptor-Ligand Interactions: A Practical Approach;* Hulme, E. C., Ed.; Oxford University Press, Oxford, 1992; Chapter 1. However, incorporation of a halogen atom (e.g. Cl, Br) at the para position of the benzyl group or in the 5-position of the spiro-indoline phenyl group of spiro[3H-indole-3,4'-piperdin]-1'-yl)carbonyl]-2-(phenylmethyl-oxy)ethyl]-2-amino-2-methylpropanamide lead to a >20-fold loss in intrinsic activity on growth hormone release from rat pituitary cells. This indicated that iodine substitution (such as with $^{125}$I) at these positions would not afford a high potency ligand. Moreover, iodine has a high degree of lipophilicity and could further alter the affinity of the ligand. Enhanced hydrophilicity (water solubility) is usually inversely related to the observed "stickiness" of the radioligand which often severely restricts its usefulness in various receptor preparations, see M. W. Cunningham, et al. In Radioisotopes in Biology: A Practical Approach; Slater, R. J., Ed.; Oxford University Press, Oxford, 1990; Chapter 6. Note in this regard that ligands bearing the methane sulfonamide group should exhibit reduced lipophilicity ($\pi$ value of NHSO$_2$CH$_3$=−1.18) compared with $^{125}$I congeners ($\pi$ value of I=1.12). See C. Hansch, et al. *J. Med. Chem.* 1973, 16, 1207. In addition the amino functionality was found to be essential for biological activity and so conjugating it with the widely used Bolton-Hunter reagent was not a viable alternative. See K. G. McFarthing, In *Receptor-Ligand Interactions: A Practical Approach;* Hulme, E. C., Ed.; Oxford University Press, Oxford, 1992; Chapter 1.

Although sulfur-35 has found widespread use in the nucleotide and peptide fields, sulfonamides incorporating sulfur-35 in high specific activity are not well known. Nevertheless, because the methanesulfonyl unit on the indoline nitrogen of the compound N-[1(R)-[(1,2-dihydro-1-methanesulfonylspiro[3H-indole-3,4'-piperidin]-1'-yl) carbonyl]-2-(phenylmethyloxy)ethyl]-2-amino-2-methylpropanamide is important for obtaining good intrinsic activity (See A. A. Patchett, et al. *Proc. Natl. Acad. Sci.* 1995, 92, 7001), it was critical to maintain such functionality. Suprisingly, however, equal activities were obtained using the benzenesulfonyl substitution on the indoline nitrogen of N-[1(R)-[(1,2-dihydro-1-methanesulfonylspiro[3H-indole-3,4'-piperidin]-1'-yl)carbonyl]-2-(phenylmethyloxy) ethyl]-2-amino-2-methylpropanamide. Initially, preparation of high specific activity benzene[$^{35}$S]sulfonyl chloride was attemptted due to the relative ease of synthesis. However, all attempts to sulfonate benzene with carrier free [$^{35}$S]sulfuric acid (obtained from NEN at 1300 Ci/mmol) were frustrated by substantial dilution of specific activity for the resulting benzene[35S]sulfonic acid. This discrepancy was apparently the result of contamination by trace amounts of ubiquitous sulfates in various reagents and/or reaction vessels. Nevertheless, preparation of high specific activity methane [$^{35}$S]sulfonyl chloride was achieved. This reagent was used to prepare the desired [35S]radioligand in high specific activity.

SUMMARY OF THE INVENTION

The instant invention is directed to [$^{35}$S]-N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide, and pharmaceutically acceptable salts thereof.

This [35S] labeled radioligand is useful in identifying and characterizing cellular receptors which play a role in the activity of growth hormone secretatogogues. In addition, this [$^{35}$S] radioligand is useful in assays which test compounds for growth hormone secretagogue activity.

DESCRIPTION OF THE INVENTION

The present invention is directed to a high specific activity sulfur-35 labeled sulfonamide radioligand and processes for its preparation. In particular, the present invention is directed to the compound [$^{35}$S]-N-[1(R)-[(1,2-dihydro-1-methanesulfonylspiro[3H-indole-3,4'-piperidin]-1'-yl) carbonyl]-2-(phenylmethyloxy)ethyl]-2-amino-2-methylpropanamide, and pharmaceutically acceptable salts thereof, in particular, the methanesulfonate salt and the hydrochloride salt.

This radiolabeled compound has the structure:

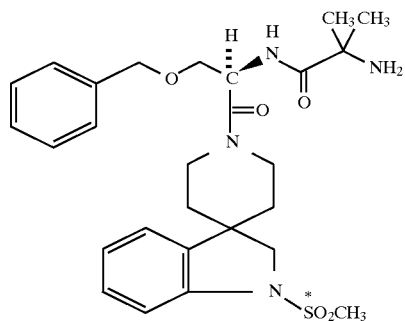

wherein * denotes the presence of a sulfur-35 atom. For convenience, this compound is also refered to as "[$^{35}$S] radioligand" herein.

This [$^{35}$S] radioligand is useful in identifying and characterizing cellular receptors which play a role in the activity of growth hormone secretatogogues, for example as disclosed in *Science*, 273, 974–977 (1996). In general, such uses comprise contacting the [$^{35}$S]radioligand with a putative growth hormone secretagogue receptor, such as a biological sample comprising the putative growth hormone secretagogue receptor, and determining whether binding has occurred. In addition, this [$^{35}$S] radioligand is useful in assays which test compounds for growth hormone secretagogue activity. Such assays generally comprise contacting a compound suspected of being a growth hormone secretagogue with a growth hormone secretagogue receptor, such as a biological sample comprising a growth hormone secretagogue receptor, in the presence of the [$^{35}$S]readioligand and monitoring whether the compound suspected of being a growth hormone secretagogue influences the binding of the [$^{35}$S]radioligand to the growth hormone secretagogue receptor.

In a preferred embodiment, the [35S]radioligand possesses a high specific activity of greater than about 700 Ci/mmol, such as about 700–1200 Ci/mmol.

The present invention further provides processes for the preparation of methane[35S]sulfonyl chloride. The instant process provides methane[$^{35}$S]sulfonyl chloride at near theoretical specific activity. Methane[$^{35}$S]sulfonyl chloride is useful in the preparation of radioligands which possess a methanesulfonamide functionality.

The process for the preparation of methane [$^{35}$S] sulfonyl chloride is outlined as follows. High specific activity sodium [$^{35}$S]sulfite is obtained by reduction of [$^{35}$S]sulfuric acid on a copper surface at approximately 200° C. with trapping of the generated [$^{35}$S]sulfur dioxide in sodium hydroxide solution. Use of the Strecker reaction (see Gilbert, E. E *Sulfonation and Related Reactions;* Wiley: New York, 1965; 136–146) gave methane[$^{35}$S]sulfonate from the sodium [$^{35}$S]sulfite. However, the sodium [$^{35}$S]sulfite was rapidly oxidized to [$^{35}$S]sulfate.

Accordingly, a one-pot reaction system was devised in which excess methyl iodide was added to the sodium hydroxide trap to directly obtain sodium methane[$^{35}$S] sulfonate (1–5% yield from [$^{35}$S]sulfuric acid) along with varying amounts of sodium [$^{35}$S]sulfate, which was readily recycled. Conversion to methane[$^{35}$S]sulfonyl chloride is preferably effected by using oxalyl chloride with dimethyl formamide in dichloromethane. See A. W. Burgstahler, et al. *Synthesis* 1976, 767. Of critical importance to the success of subsequent reaction with an amino functionality, excess oxalyl chloride is removed by washing the dichloromethane solution with aqueous 0.5% sodium bicarbonate solution. This is accompanied by small amounts of methane[$^{35}$S] sulfonyl chloride hydrolysis (10–15%). The solution is then dried over sodium sulfate and concentrated by atmospheric distillation.

Accordingly, the instant process for the preparation of methane[$^{35}$S]sulfonyl chloride comprises:

(1) reduction of [$^{35}$S]sulfuric acid on a copper surface to generate [$^{35}$S]sulfur dioxide;

(2) exposing the generated [$^{35}$S]sulfur dioxide to an aqueous solution of sodium hydroxide solution and methyl iodide to give sodium methane[$^{35}$S]sulfonate;

(3) contacting the sodium methane[$^{35}$S]sulfonate with a solution of oxalyl chloride and dimethyl formamide in dichloromethane; and (4) washing the dichloromethane solution with aqueous sodium bicarbonate solution to give methane[$^{35}$S]sulfonyl chloride.

The methane[$^{35}$S]sulfonyl chloride generated by the foregoing process may be readily employed in the preparation of [$^{35}$S]-N-[1(R)-[(1,2-dihydro-1-methanesulfonylspiro[3H-indole-3,4'-piperidin]-1'-yl)carbonyl]-2-(phenylmethyloxy) ethyl]-2-amino-2-methylpropanamide as depicted in Scheme I.

SCHEME I:

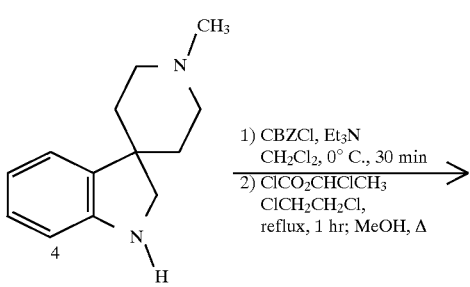

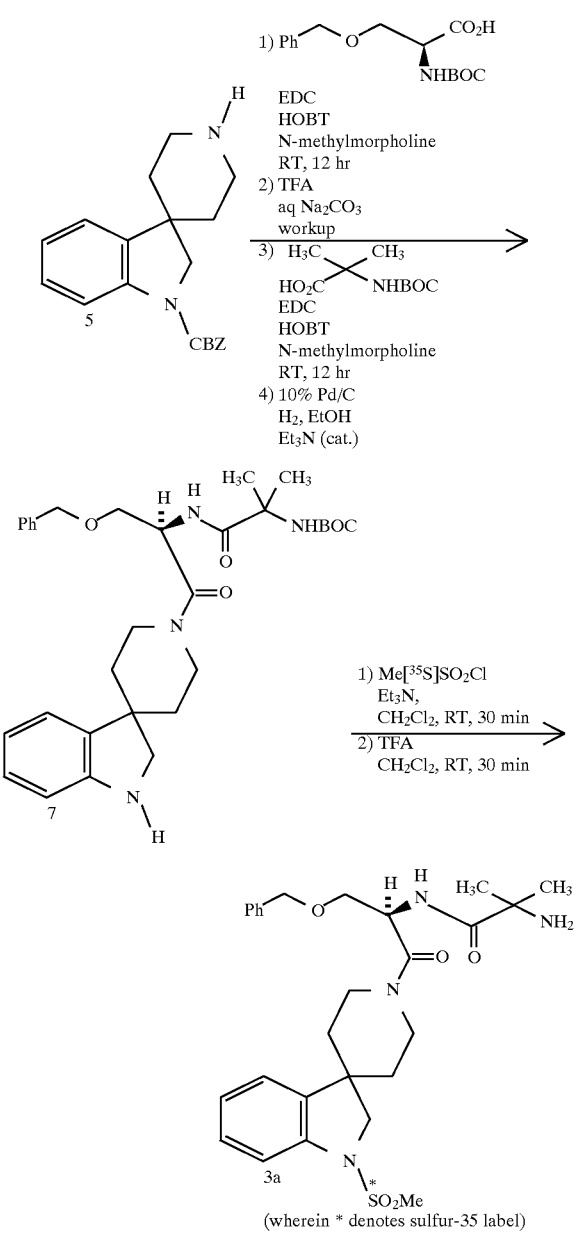

(wherein * denotes sulfur-35 label)

The process previously disclosed in the art for the preparation of N-[1(R)-[(1,2-dihydro-1-methanesulfonylspiro [3H-indole-3,4'-piperidin]-1'-yl)carbonyl]-2-(phenylmethyloxy)ethyl]-2-amino-2-methylpropanamide commenced with an appropriate spiro-indoline sulfonamide. See U.S. Pat. No. 5,536,716, PCT Patent Publication WO 94/13696 and *Proc. Natl. Acad. Sci. USA,* 92, 7001–7005 (July 1995). However, for the expedient preparation of the the desired [$^{35}$S]sulfonamide radioligand, a new synthesis of N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide was designed wherein the sulfonyl unit was incorporated in the penultimate step. Protection of the known spiroindoline 4 as a benzyloxycarbamate followed by N-demethylation according to the procedure of Olofson (see R. A. Olofson, et al. *J. Org. Chem.* 1984, 49, 2081) gave the spiropiperidine 5 in 80% yield. Standard peptide type coupling of 5 with O-benzyl-D-serine 6, removal of the BOC protecting group with strong acid, followed by a second coupling with N-t-BOC-aminoisobutyric acid and subsequent selective hydrogenolysis of the N-CBZ group (Pd/C in ethanol contaning a trace of triethylamine) gave the intermediate amine 7 in excellent yield. In the interest of efficiency, it is preferred that these reaction steps be conducted in situ without isolation of the compounds following their preparation by the subject processes.

Optimal conditions for sulfonylation of 7 consisted of adding a maximally concentrated methane[$^{35}$S]sulfonyl chloride solution to a near saturated solution of 7 in dichloromethane in the presence of triethylamine. The instantaneous reaction typically produced the desired [$^{35}$S] sulfonamide in 60–70% radiochemical yields. The remaining radioactivity corresponded to methane[$^{35}$S] sulfonic acid, formed through hydrolysis by residual water in the presence of amine base. The utilization of more dilute solutions of 7 resulted in almost exclusive formation of the sulfonic acid. Subsequent BOC removal and HPLC purification produced [$^{35}$S]-3a of >99% radiochemical purity.

Determination of [$^{35}$S]radioligand specific activity by standard UV/concentration measurement proved difficult and unreliable. However, accurate values were readily obtained using $\mu$Ci amounts of radioligand by capillary LC/MS/MS analysis to directly observe the isotopic ratio of $^{32}$S/$^{35}$S. Specific activities ranging from about 700–1200 Ci/mmol were obtained using different batches of methane [$^{35}$S]sulfonic acid, presumably a consequence of variable isotopic purity of [$^{35}$S]sulfate precursor and/or contamination during the preparation of this reagent.

The [$^{35}$S]-radioligand demonstrated remarkable stability (<0.5% loss of radiochemical purity/month) when stored at −20° C. as a solution in 15% methanol/water solution containing a trace of hydrochloric acid.

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography. The following examples are provided for the purpose of further illustration only and are not intended to be limitations on the disclosed invention.

EXAMPLE 1

Sodium methane [$^{35}$S]sulfonate

To a solution of sodium [$^{35}$S]sulfite (1 Ci/mmol, 215 uCi in 100 uL of 0.1N NaOH solution with 10 mM DTT and 1 mM EDTA) (which may be obtained by reduction of [$^{35}$S] sulfuric acid on a copper surface with trapping of the generated [$^{35}$S]sulfur dioxide in sodium hydroxide solution) was added 25 uL of methyl iodide and the reaction was stirred at room temperature for 20 min. Analysis of radioactivity by HPLC (Astec cyclobond I column, gradient of 10 mM nitric acid solution to 180 mM nitric acid solution over 20 min, 1 mL/min) indicated complete conversion to methane[$^{35}$S]sulfonic acid. The solution was concentrated under nitrogen to near dryness, 500 uL of DI water was added, and the solution was degassed with nitrogen. The resulting solution of sodium methane[$^{35}$S]sulfonate (177 uCi) was stored at 0° C.

EXAMPLE 2

Methane [$^{35}$S]sulfonyl chloride

A solution of methane[$^{35}$S]sulfonic acid (3.37 mCi in 2.08 g of 0.1N sodium hydroxide, specific activity=1342 Ci/mmol, approx 90% RCP, obtained from New England Nuclear) was blown to dryness under a stream of nitrogen at 50° C. To the resulting residue was added dichloromethane (1 mL) followed by oxalyl chloride (100 uL, 0.54 mmol). Vigorous gas evolution occurred for about 1.5 hr, at which point addition of additional oxalyl chloride (20 uL) did not produce any visible reaction. A 10% solution of dimethylformamide in dichloromethan (20 uL) was added which resulted in a change in color to greenish yellow. Addition of oxalyl chloride (20 uL, 0.761 mmol total) did not produce visible reaction and the reaction mixture was stirred at 0° C. for 12 hr. The mixture was allowed to warm to room temperature, diluted with dichloromethane (3 mL), counted (2.37 mCi), and washed with 5% sodium bicarbonate solution (2×1 mL) followed by 2% sodium bisulfite solution (1 mL). The dichloromethane solution was dried over sodium sulfate. Measurement of the radioactivity by counting the resulting solution indicated 1.75 mCi (approx 58% yield) to be present.

EXAMPLE 3

1,2-Dihydro-1-benzyloxycarbonyl-spiro[3H-indole-3,4'-piperdine] hydrochloride

To a solution of 99g (0.489 mol) of N'-methyl spiro (indoline-3,4'-piperidine) (i.e. 1'-methyl-1,2-dihydro-spiro [3H-indole-3,4'-piperdine]) (prepared according to the method of Ong et al. *J. Med. Chem.* 1983, 26, 981–986) in 1 L of dichloromethane was added 82 mL (0.588 mol) of triethylamine and the reaction was cooled to 0C. CBZ-Cl (77 mL; 0.539 mol) was added in a dropwise manner over 30 min and the temperature was maintained below 10° C. After 2 h an additional 19 mL of triethylamine and 5 mL of CBZ-Cl were added and stirred for 2 h. Analysis of the reaction mixture showed a small amount of the starting material and so additional 19 mL of triethylamine and 15 mL of CBZ-Cl were added and stirred for 2 h. The volatiles were removed on the rotary evaporator and the residue was taken up in ether (1000 mL) and washed with 500 mL of saturated aqueous sodium bicarbonate solution. The aqueous layer was extracted with 500 mL of ether and the combined organics were washed with 500 mL of saturated aqueous sodium bicarbonate solution, 500 mL of brine, dried over anhydrous magnesium sulfate and concentrated. The residue was chromatographed on 2 kg of silica gel and eluted with 2.5% methanol/CH$_2$Cl$_2$ with increasing polarity to 5% methanol/CH$_2$Cl$_2$ to give 117 g (71%) of the desired material as a yellow oil.

To a solution of 117 g (0.348 mol) of the above N-methyl spiro-piperidine in 800 mL of 1,2-dichloroethane at 0° C. was added 50 mL (0.463 mL) of 1-chloroethyl chloroformate over 20 min. and the reaction mixture was heated at reflux for 1 h. The reaction mixture was cooled, concentrated to approximately ¼th of the original volume, diluted with 700mL of methanol and refluxed for 1.5 h. The rection mixture was concentrated to dryness, the residue was washed with cold methanol, followed by ether and dried under vacuum to 75.3 g of a brown solid. The filtrate was concentrated to give a brown foam (58 g). The solid and the foam were taken up in dichloromethane and washed with 2.5N sodium hydroxide till basic. The organic layer was dried over anhydrous magnesium sulfate, filtered and concentrated to provide a residue that was chromatographed on 2 kg of silica gel. Elution with 20 liters of 5% methanol/CH$_2$Cl$_2$ followed by 20 liters of 90/10/1 methanol/CH$_2$Cl$_2$/NH$_4$OH provided 91.26 g of the piperidine and 14.84 g of recovered starting material. A solution of the above piperidine (91.26 g) in 1000 mL of ethyl acetate containing a trace of methanol was treated with dry HCl (gas) till the reaction mixture was acidic. The reaction mixture was concentrated to dryness and the foamy residue was triturated with ether to give 91.5 g (73%) of the subject piperidine hydrochloride salt as a pale yellow solid.

EXAMPLE 4

N-[1(R)-[(1,2-Dihydro-1-benzyloxycarbonyl-spiro [3H-indole-3,4'-piperdin]-1'-yl)carbonyl]-2- (phenylmethyloxy)-ethyl]-2-[(1,1-dimethylethyloxy) carbonyl]amino]-2-methylpropanamide To 5 g of 1,2-dihydro-1-benzyloxycarbonyl-spiro[3H-indole-3,4'-piperdine] hydrochloride in 100 mL of dichloromethane at room temperature was added 3.64 g of N-tBOC-O-benzyl-D-serine, 1.83 g of HOBT, 2.60 mL of N-methylmorpholine, and 3.70 g of EDC and stirred for 18 h. The reaction mixture was poured into 100 mL of water and extracted with $CH_2Cl_2$ (2×100 mL). The combined organics were washed with 100 mL of 10% citric acid, 100 mL of saturated $NaHCO_3$, dried over $MgSO_4$, and concentrated. To a solution of the intermediate in 20 mL of $CH_2Cl_2$ was added 20 mL of trifluoroacetic acid and stirred at RT for 30 min. The reaction mixture was concentrated, diluted with 50 mL of dichloromethane and carefully basified with 100 mL of 10% aqueous sodium carbonate solution. The organic layer was separated and the aqueous layer was further extracted with 2×50 mL of dichloro-methane. The combined organics were washed with 50 mL of water, dried over potassium carbonate, filtered and concentrated to give the amine as a thick oil. To the above intermediate in 50 mL of dichloromethane at room temperature was added 2.50 g of N-tBOC-α-methylalanine, 1.83 g of HOBT, and 3.70 g of EDC and stirred for 18 h. The reaction mixtured was poured into 10 mL of water and extracted with $CH_2Cl_2$ (2×10 mL). The combined organics were washed with 20 mL of 10% citric acid, 20 mL of saturated $NaHCO_3$, dried over $MgSO_4$, and concentrated. Flash chromatography of the residue over 300 g of silica gel with hexane-ethyl acetate (2:1) as eluent gave 8.1 g of product $^1H$ NMR (400MHz, $CDCl_3$) δ7.85(bs, 1H), 7.45–7.20 (m, 10H), 7.20–7.05 (m, 22/3H), 6.95 (t, 1/3H), 6.88(t, 1/3H), 6.53 (dd, 2/3H), 5.35–5.20 (m, 2H), 5.20–5.10 (m, 1H), 4.92 (bs, 1H), 4.65–4.20 (m, 4H), 4.05 (bd, 2/3H), 4.00–3.80 (m, 1,1/3H), 3.80–3.60 (m, 1H), 3.10 (t, 2/3H), 3.00–2.85 (m, 1/3H), 2.82–2.60 (2t, 1H), 1.90–1.55 (m, 5H), 1.49 (s, 4H), 1.42 (s, 2H), 1.40 (s, 9H).

EXAMPLE 5

N-[1(R)-[(1,2-Dihydro-spiro[3H-indole-3,4'-piperdin]-1'-yl)carbonyl]-2-(phenylmethyloxy)ethyl] -2-[(1,1-dimethylethoxy)carbonyl]amino]-2-methylpropanamide To a solution of 8.10 g of N-[1(R)-[(1,2-Dihydro-1-benzyloxycarbonyl-spiro[3H-indole-3,4'-piperdin]-1'-yl) carbonyl]-2-(phenylmethyloxy)-ethyl]-2-[(1,1-dimethylethoxy)carbonyl]amino]-2-methylpropanamide obtained from the previous example in 80 mL of ethanol was added 1 g of 20% palladium hydroxide/C and hydrogenated with hydrogen balloon for 1 h. The catalyst was filtered off through a pad of celite and washed with ethyl acetate. The filtrate was concentrated to give 4.69 g of the product as a colorless foam. $^1H$ NMR (400MHz, $CDCl_3$) δ7.35–7.20 (m, 5H), 7.18 (d, 1/2H), 7.10 (d, 1/2H), 7.04–6.98 (m, 2H), 6.75–6.60 (m, 2H), 5.20–5.10 (m, 1H), 4.97 (bs, 1H), 4.55–4.40 (m, 3H), 3.95 (dd, 1H), 3.73–3.61 (m, 1H), 3.60–3.50 (m, 1H), 3.50–3.33 (m, 3H), 3.10 (dt, 1H), 2.83 (dt, 1H), 1.85–1.55 9m, 5H), 1.47 (s, 4H), 1.42 (s, 2H), 1.39 (s, 9H).

EXAMPLE 6

[$^{35}S$]N-[1(R)-[(1,2-Dihydro-1-methanesulfonylspiro [3H-indole-3,4'-piperdin]-1'-yl)carbonyl]-2- (phenylmethyloxy)ethyl]-2-amino-2- methylpropanamide A solution of methane [$^{35}S$]sulfonyl chloride (1.5 mCi) in dichloromethane was carefully concentrated via atmospheric distillation in a pear-shaped flask to a minimal volume (~100 uL). This concentrate was added to a mixture of N-[1(R)-[(1,2-dihydro-spiro[3H-indole-3,4'-piperdin]-1'-yl)carbonyl]-2-(phenylmethyloxy)ethyl]-2-[(1,1 -dimethylethoxy)carbonyl]amino-2-methyl-propanamide (10 mg) and triethylamine (5 uL) in 20 uL of dichloromethane at room temperature. The distillation flask was rinsed with dichloromethane (2×100 uL) which was added to the amine solution. The mixture was stirred at room temperature for 15 min at which point analysis by HPLC (RX-C8 column, 30% MeCN–0.1% Aq TFA to 100% MeCN over 30 min, 1 mL/min, radioactivity flow monitor) indicated ~70% N-BOC [$^{35}S$]radioligand (rt =20 min) along with ~30% methane [$^{35}S$]sulfonic acid. The reaction mixture was diluted with 0.5 mL of dichloromethane, washed with saturated sodium bicarbonate solution (2×0.5 mL) and dried over sodium sulfate. Measurement of the radioactivity by counting the resulting solution indicated 950 uCi (63% yield) to be present with a radiochemical purity of 93% by HPLC analysis (above system). The solution of N-BOC [$^{35}S$]radioligand was concentrated to ~1 mL under a stream of nitrogen at 40° C. and dimethyl sulfide (100 uL), followed by trifluoroacetic acid (300 uL) were added. The mixture was stirred at room temperature for 1 h at which point analysis by HPLC (above system) indicated complete conversion to [$^{35}S$]radioligand (rt=10.5 min). The mixture was concentrated in vacuo to near dryness and the resulting residue partitioned between 1% sodium bicarbonate solution (2 mL) and dichloromethane (3 mL). After vigorous stirring, the dichloromethane layer was separated and dried over sodium sulfate. Measurement of the radioactivity by counting the resulting solution indicated 835 uCi (~88% yield) of [$^{35}S$]N-[1(R)-[(1,2-dihydro-1-methanesulfonylspiro[3H-indole-3,4'-piperdin]-1'-yl) carbonyl]-2-(phenylmethyloxy) ethyl]-2-amino-2-methylpropanamide to be present with a radiochemical purity of 92%.

Purification was effected by sequential preparative HPLC with attached radioactivity detector using: (1) an RX-C8 column (9.4 mm×25 cm, 500 uL loop) eluting with a gradient system of 50% MeCN–0.1% Aq. TFA to 70 % MeCN over 30 min at a flow rate of 3.5 mL/min (rt=~24 min) followed by (2) an PRP-1 column (4.6 mm×25 cm, 200 uL loop) eluting with a gradient system of 50% MeOH—water with 1 mM HCl to 90% MeOH—water with 1 mmol HCl over 30 min at a flow rate of 1 mL/min (rt=~22 min). Analysis of ~20 uCi of the radioligand by capillary LC/MS indicated a 10:3.5 ratio of $^{35}S/^{32}S$ corresponding to a specific activity of 1110 Ci/mmol.

EXAMPLE 7

Measurement of [$^{35}S$]N-[1(R)-[(1,2-Dihydro-1-methanesulfonylspiro [3H-indole-3,4'-piperdin]-1'-yl) carbonyl]-2-(phenylmethyloxy)ethyl]-2-amino-2-methylpropanamide Binding to Porcine and Rat Pituitary Membranes Anterior lobes of the pituitary were removed from male swine (50–80 Kg) in 12–30 min after sacrifice of animals or from the Wistar male rats (150–200 g) immediately after decapitation. The pituitary tissues were either immediately used or stored at −80° C. Fresh or defrosted pituitary glands were homogenized in a motor driven tissue homotenizer with a teflon pestle in ice-cold buffer (50 mM Tris-HCl buffer, pH 7.4 containing 5 mM $MgCl_2$, 2.5 mM EDTA, 0.1% bovine serum albumin and 30 μg/ml bacitracin). The homogenates were centrifuged for 5 min at 1,400×g. The supernatants were then centrifuged at 34,000×g for 20 min. The pellets (membrane-enriched fractions) were resuspended in same buffer to a 1,500 μg protein/ml. The aliquotes of the suspensions were stored at −80° C. up to five weeks without significant lose of the binding activity. Protein was determined by a Bio-Rad method using bovine serum albumin as a standard. Binding assays were performed as follows: standard binding solution contained: 400 microliter of 25 mM Tris-HCl buffer, pH 7.4, 10 mM MgCl2, 2.5 mM EDTA, and 100 pM [$^{35}$S]N-[1(R)-[(1,2-Dihydro-1-methanesulfonylspiro [3H-indole-3,4'-piperdin]-1'-yl) carbonyl]-2-(phenylmethyloxy)ethyl]-2-amino-2-methylpropanamide. Pituitary membranes (100 microliter, 150 μg protein) were added to initiate the binding reaction. Aliquots were incubated at 20° C. for 60 min and bound radioligand was separated from free by vacuum filtration through GF/C fiberglass filters pretreated with 0.5% of polyethylenimine in a 24-channel Brandel cell harvester. The filters were then rapidly washed three times with 3-ml of ice-cold buffer (50 mM Tris-Hcl, pH 7.4, 10 mM MgCl2, 2.5 mM EDTA and 0.015% Triton X-100) and the amount of radioactivity on the filters were counted in Aquasol 2. Specific binding was defined as the difference between total binding and binding in the presence of 500 nM unlabeled N-[1(R)-[(1,2-Dihydro-1-methanesulfonylspiro [3H-indole-3,4'-piperdin]-1'-yl) carbonyl]-2-(phenylmethyloxy)ethyl]-2-amino-2-methylpropanamide. This compound may be prepared as described in U.S. Pat. No. 5,536,716, PCT Patent Publication WO 94/13698 and Proc. Natl. Acad. Sci. USA, 92, 7001–7005 (July 1995). Nonspecific binding and specific binding were 15–35 and 40–55% of total binding, in procine and rat membranes, respectively. Assays were carried out in triplicate and experiments repeated at least three times. Saturation experiments were performed by incubating a fixed concentration of membranes (150 μg protein) with various concentrations of [$^{35}$S]N-[1(R)-[(1,2-Dihydro-1-methanesulfonylspiro [3H-indole-3,4'-piperdin]-1'-yl) carbonyl]-2-(phenylmethyloxy)ethyl]-2-amino-2-methylpropanamide (20–2,000 pM). Saturation isotherm of specific [$^{35}$S]N-[1(R)-[(1,2-Dihydro-1-methanesulfonylspiro [3H-indole-3,4'-piperdin]-1'-yl) carbonyl]-2-(phenylmethyloxy)ethyl]-2-amino-2-methylpropanamide binding were analyzed by Scatchard analysis.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound which is selected from:

[$^{35}$S]-N-[1(R)-[(1,2-dihydro-1-methanesulfonylspiro[3H-indole-3,4'-piperidin]-1'-yl)carbonyl]-2-(phenylmethyloxy)ethyl]-2-amino-2-methylpropanamide, and pharmaceutically acceptable salts thereof.

2. The compound of claim 1 which is present as the hydrochloride salt.

3. The compound of claim 1 which is present as the methanesulfonate salt.

4. The compound of claim 1 which possesses a specific activity of greater than 700 Ci/mmol.

5. The compound of claim 1 which possesses a specific activity of about 700–1200 Ci/mmol.

6. A compound of the formula:

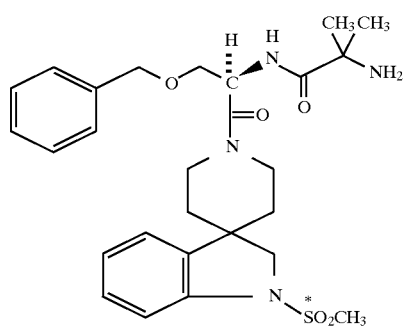

wherein * denotes the presence of a sulfur-35 atom, and pharmaceutically acceptable salts thereof.

7. The compound of claim 6 which is present as the hydrochloride salt.

8. The compound of claim 6 which is present as the methanesulfonate salt.

9. The compound of claim 6 which possesses a specific activity of greater than 700 Ci/mmol.

10. The compound of claim 6 which possesses a specific activity of about 700–1200 Ci/mmol.

11. A method of identifying a cellular receptor as a growth hormone secretagogue receptor comprising contacting the cellular receptor with the compound of claim 1 and determining whether binding has occurred.

12. A method for identifying the activity of a compound as a growth hormone secretagogue comprising contacting the compound suspected of having activity as a growth hormone secretagogue with a growth hormone secretagogue receptor in the presence of the compound of claim 1 and monitoring whether the compound suspected of having activity as a growth hormone secretagogue influences the binding of the compound of claim 1 to the growth hormone secretagogue receptor.

* * * * *